United States Patent [19]

Loschiavo

[11] Patent Number: 4,927,635
[45] Date of Patent: May 22, 1990

[54] DEVICE FOR CONTROLLING STORED FOOD INSECTS

[75] Inventor: Samuel R. Loschiavo, Winnipeg, Canada

[73] Assignee: Canadian Patents & Development Ltd., Ottawa, Canada

[21] Appl. No.: 222,571

[22] Filed: Jul. 21, 1988

[30] Foreign Application Priority Data

Jul. 24, 1987 [CA] Canada .................. 543006

[51] Int. Cl.⁵ .............................. A01N 25/08
[52] U.S. Cl. .............................. 424/409; 424/405; 424/407; 424/410; 424/84; 424/416
[58] Field of Search .............. 424/416, 84, 409, 407, 424/411, 77, 405; 252/315.6

[56] References Cited

U.S. PATENT DOCUMENTS 2,911,756  11/1959  Geary .................. 424/416
3,661,838   5/1972  Enomoto .............. 424/416
4,317,836   3/1982  Chuman et al. ....... 424/84

FOREIGN PATENT DOCUMENTS 0005307  of 1890  United Kingdom ...... 424/416
0654029  5/1951  United Kingdom ...... 424/416

OTHER PUBLICATIONS

W. Ebeling, 1961, Physicochemical Mechanisms for the Removal of Insect Wax by Means of Finely Divided Powders, Hilgardia, 30:531-564.
W. Ebeling and R. E. Wagner, 1961, Relation of Lipid Adsorptivity of Powders to Their Suitability as Insecticide Ailments, Hilgardia, 30:565-586.
W. Ebeling, 1971, Sorptive Duets for Pest Control, Annual Review of Entomology, 16:123-158.

Primary Examiner—Thurman K. Page
Assistant Examiner—P. L. Prater
Attorney, Agent, or Firm—Juliusz Szereszewski

[57] ABSTRACT

This invention relates to a device for controlling certain common insect pests of stored food products in human residences, food storages and the like. It comprises, generally, a substrate, such as paper, cardboard or plastic and a deposit of silica aerogel particles releasably bonded to the substrate. The strength of the bond prevents the silica aerogel particles from being released by air currents but allows the particles to be picked up by some insects that contact the deposit.

8 Claims, 1 Drawing Sheet

DEVICE FOR CONTROLLING STORED FOOD INSECTS

This invention relates to a device for controlling certain common insect pests of stored food products in human residences, food storages and the like.

DESCRIPTION OF PRIOR ART

Certain insects are pernicious pests of stored food products such as cereals, nuts, seeds, dried fruits, cake and confection products etc. stored in human residences, food storages or similar areas. Common insect pests are the confused flour beetle, *Tribolium confusum* Duv. and the merchant grain beetle, *Oryzaephilus mercator* Fauvel. The latter is widespread as a household pest, particularly in multiple dwelling buildings where the insect can migrate between units via pipe chases, ducts, crevices etc.

Several insect control methods and devices have been used and known thus far. Fumigation, or gassing of infected areas is still widely used. It is commonly known to attract and trap insects on a sticky surface of a bait dispenser, such as a fly trap.

Various insecticides, usually adopted to control a particular strain or species, are often employed, sometimes mixed with attractants. U.S. Pat. No. 4,227,333 granted Oct. 14, 1980 to H. Levinson et al. discloses a device comprising fibrous fabric or paper strips forming a trap provided with living agents and insecticides. Accumulation of larvae and adult insects, viz. Khapra beetles, is also promoted, beside the attractants, by the thigmotactic stimuli provided by the fibrous substance of the trap.

For use in residential areas, fumigation or gassing with pesticides has many environmental drawbacks. It is also known that insects can develop resistance to the insecticide used and this phenomenon can cause serious rebound problems.

Silica gel, particularly amorphous fine silica gel, is known for its insecticidal properties. It is effective to control various insects such as some beetles, cockroaches, mites, termites. It may be applied in a dust form, e.g. by spraying in relatively low concentrations. Its insecticidal effect is due to biochemical action (selective adsorption of cuticular lipid) and mechanical action (death by desiccation) depending on which part of the insect body comes in contact with silica gel particles. Owing to the above-described mechanism, there is virtually no danger of insects developing resistance to silica gel.

However, the physical properties of silica gel, especially the small size of its particle aggregates (about 3 microns) make its use troublesome in residential areas. The particles float in the slightest air currents and thus may easily be inhaled by humans or domestic animals. Thus, the use of silica aerogel (silica gel in powder form) should be discouraged based on the present knowledge of related health hazards.

Another objection to dust formulations is that in still air, silica gel aggregates would settle on furniture, floors, counter tops etc. leaving an objectionable grey haze or film.

In view of the above, this invention is aimed at utilizing the advantageous properties of silica gel in its powder, or dust form while eliminating the associated drawbacks and inconveniences.

STATEMENT OF INVENTION

According to the invention, there is provided a device for controlling crawling household or stored product insects, particularly in residential areas. The device comprises, in general, a substrate and a deposit of fine silica gel particles releasably secured to the substrate. A binding means may be provided to ensure a releasable bond between the substrate layer and the deposit. Preferably, the binding means is an adhesive, particularly a substantially permanent adhesive. The deposit of silica gel particles may be applied on a variety of substrates, preferably paper, burlap, cardboard or porous plastic.

BRIEF DESCRIPTION OF DRAWING

The invention is illustrated in a single drawing showing in cross-section an embodiment of the device for controlling insects.

DESCRIPTION OF PREFERRED EMBODIMENTS

Figure 1:
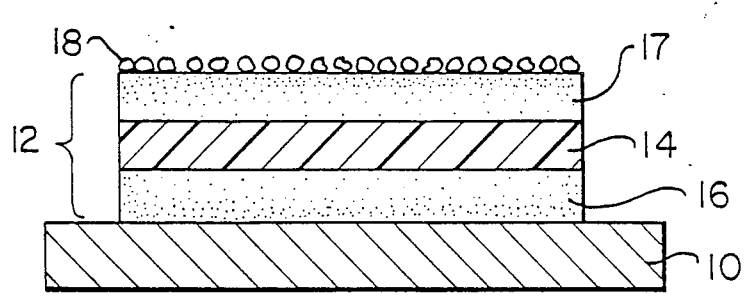

In the drawing, a strip of paper 10 forms a layer to which is secured a double-coated tape 12 consisting of a plastic film 14 and two layers of non-drying adhesive 16 and 17. As clearly seen in the drawing, the tape 12 is secured to the paper strip 10 with one adhesive layer 16. A deposit of silica aerogel particles 18 is applied onto the other adhesive layer 17.

In this embodiment, the silica aerogel is amorphous silica gel known as Dri-Die TM, or SG-67, a product of Fairfield American Corporation. According to the specification, the aerogel contains amorphous silica gel—95%, ammonium silicofluoride—2% and inert ingredients—3%. The aggregates of silica gel particles have an average size of about 3 microns while the particles in the aggregates are 0.01 to 0.05 microns in diameter.

In another embodiment of the invention, not illustrated in the drawing, a single layer of adhesive is applied onto the substrate by spraying and a deposit of silica aerogel particles in one or more layers is applied onto the single adhesive layer.

EXPERIMENTAL

In the experiments, paper, burlap, corrugated cardboard strips or porous plastic sheets were used as substrates and were found equally suitable.

Two types of binding means were used, all of them products of 3M Canada Inc. (a subsidiary of the U.S. parent company). The first type comprised 415 and 666 double-coated film tapes (Table 1).

The second type of binding means comprises three aerosol-type spray adhesives as described in Table 2.

TABLE 1

CHARACTERISTICS OF THE DOUBLE-COATED TAPES USED

| Product symbol | 415 | 666 |
|---|---|---|
| Adhesive type | A-40 medium-firm acrylic | |
| Adhesive carrier | Polyester film | UPVC film |
| Release liner | Tan paper | PE film |
| Temperature operating range | | |
| long term (days) | 65° C. | 52° C. |
| short term (minutes, hours) | 82° C. | 52° C. |
| Approximate thickness | | |
| film | 0.025 mm | 0.025 mm |

TABLE 1-continued

CHARACTERISTICS OF
THE DOUBLE-COATED TAPES USED

| adhesive | 0.10 mm | 0.09 mm |
|---|---|---|

TABLE 2

CHARACTERISTICS OF THE SPRAY ADHESIVES USED

| Product symbol | 74 | 75 | 77 |
|---|---|---|---|
| Base | synthetic elastomer | synthetic elastomer | SBR (styrene butadiene rubber) |
| Solvent | chlorinated & aliphatic | chlorinated | hexane and cyclohexane |
| Solids content wt. % | 10 | 9 | 25 ± 2 |
| Bond type | strong flexible | temporary flexible | strong flexible |

In this specification, tests conducted on two species of beetles commonly found in residences, the merchant grain beetle (*Oryzaephilus mercator*) and the confused flour beetle (*Tribolium confusum*) are reported. In the tests reported herein, results obtained using the spray adhesives (Table 2) are indicated.

*Oryzaephilus mercator*. Groups of insects were exposed for 3 hours and for 24 hours respectively to fresh or "old" deposits of silica aerogel (Dri-Die) on paper coated with 74, 75 and 77 adhesives respectively (see Table 2). The mortality results for these insects are indicated in Table 3.

TABLE 3

MORTALITY OF O. MERCATOR EXPOSED TO
LIGHT DEPOSITS (0.15–0.18 MG/CM$^2$) OF DRI-DIE

| | Mean number dead* out of 20 | | | | | | | | | |
|---|---|---|---|---|---|---|---|---|---|---|
| | 3-hour exposure | | | | | 24-hour exposure | | | | |
| | Age of deposit, days | | | | | | | | | |
| | 0 | 7 | 14 | 21 | 35 | 0 | 7 | 14 | 21 | 35 |
| 74 adhesive (0.17 mg/cm$^2$) | 20 | 20 | 19 | 18 | 7 | 20 | 20 | 20 | 20 | 20 |
| 75 adhesive (0.17 mg/cm$^2$) | 20 | 20 | 11 | 9 | 2 | 20 | 20 | 20 | 20 | 20 |
| 77 adhesive (0.15 mg/cm$^2$) | 7 | 6 | 2 | 2 | 1 | 20 | 20 | 20 | 20 | 7 |

*Figures rounded to nearest unity

Additional tests were conducted with heavier deposits of Dri-Die (0.55 to 0.59 mg/cm$^2$) on all adhesives. The results are shown in Table 3A.

TABLE 3A

MORTALITY (%) OF O. MERCATOR
EXPOSED FOR 3 HOURS OR 24
HOURS TO HEAVY (0.55-0.59
MG/CM$^2$) DEPOSITS OF DRI-DIE
42 DAYS OLD ON PAPER
COATED WITH 74.75 OR 77 ADHESIVES

| Adhesive | Time of exposure, hours | Mortality % |
|---|---|---|
| 74 | 3 | 100 |
| 75 | 3 | 100 |
| 77 | 3 | 100 |
| 77 | 24 | 100 |

Groups of adult *O. mercator* beetles were immersed in Dri-Die for about 5 seconds, then cleaned in water or air stream and placed in containers with and without food. The mortality results are presented in Table 4.

A series of tests was conducted to determine the effect of food after a 30-second exposure of *O. mercator* to a surface layer of Dri-Die applied on a filter paper coated with a spray adhesive. The mortality results are presented in Table 5.

TABLE 4

MORTALITY OF ADULT MERCHANT
GRAIN BEETLES 24 HOURS AFTER
THEY WERE IMMERSED IN SG-67,
CLEANED IN AN AIR STREAM
OR WATER, AND THEN PLACED IN
CONTAINERS WITH AND WITHOUT FOOD

| Treatment | Time of exposure, sec | Mean[1] (±SE) within 24 h after exposure | |
|---|---|---|---|
| | | Without food | With food |
| SG-67 | 5 | 100 (0) | 29.7 (0.88) |
| | 15 | 100 (0) | 24.3 (2.33) |
| SG-67 + air | 5 | 100 (0) | 9.0 (3.06) |
| | 15 | 100 (0) | 11.0 (1.00) |
| SG-67 + water rinse | 5 | 8.0 (0.58) | 0.3 (0.33) |
| | 15 | 11.0 (2.33) | 1.3 (0.33) |
| Air | 15 | 2.0 (1.00) | 0 (0) |
| Water rinse | 15 | 0.7 (0.33) | 0 (0) |
| No treatment | 15 | 0.3 (0.33) | 0 (0) |

[1]100 adults in each of 3 replicates. Two-way ANOVA and t-tests done on transformed data. Difference due to treatment F = 1115.45; difference due to foods F = 2720.33; difference due to time of exposure F<3.31; t-values for differences due to foods ranged from 6.17 to 103.06.

TABLE 5

MORTALITY OF ADULT MERCHANT
GRAIN BEETLES EXPOSED FOR
30 SEC TO A SURFACE LAYER
OF SG-67 ADHERING TO
FILTER PAPER COATED
WITH AN ELASTOMER ADHESIVE

| Treatment | Mean no. (±SE) on surface | Mortality | | | |
|---|---|---|---|---|---|
| | | 24 h | | 48 h | |
| | | Mean[1] (±SE) | % | Mean[1] (±SE) | % |
| | No food provided after treatment | | | | |
| SG-67 | 63.3[2] (3.28) | 50.0 (5.023) | 78 | 10.3 (1.2) | 100 |
| Control | 99.0 (1.00) | 0 (0) | 0 | 1.0 (0.58) | 1 |
| | Food provided after treatment | | | | |
| SG-67 | 88.3[2] (3.28) | 10.3 (0.33) | 11 | 4.7 (0.67) | 17 |
| Control | 99.7 (0.33) | 0 (0) | 0 | 0 (0) | 0 |

[1]100 adults in each of 3 replicates. Two-way ANOVA and t-tests done on transformed data. For comparison of mortality between beetles given food or deprived of food after treatment F = 81.00 and 357.00 at 24 and 48 h, respectively; t = 9.00 and 18.89 at 24 and 48 h, respectively.
[2]No. of beetles on treated surface for 30 sec.

CONCLUSIONS

Deposits of Dri-Die on 74 and 75 adhesive are highly effective and long lasting against adults of the merchant grain beetle (*Oryzaephilus mercator*) exposed for 24 hours. Even at relatively short exposures of 3 hours, 100% mortality will occur on deposits not older than 7 days.

Light deposits (Table 3) on 77 provide 100% mortality only at exposures of 24 hours and only on deposits 0 to 21 days old. However, heavier deposits on all adhesives provide 100% mortality even when the deposits are 6 weeks old (Table 3A).

*O. mercator* is highly susceptible to the Dri-Die in dust form. Exposure to the dust for as little as 5 seconds caused 100% mortality. However, if food is provided after the exposure, mortality is drastically reduced, probably due to removal of dust particles on body and ability to restore water lost due to selective adsorption of lipids from the epicuticle (Table 4).

Dri-Die on an elastomer adhesive causes 100% mortality within 48 hours after a 30-second exposure of adult *O. mercator*. If food is provided after treatment, mortality is only 17%.

*Tribolium confusum*. Groups of insects were exposed for 3 hours and 24 hours respectively to fresh and old deposits of silica aerogel (Dri-Die) on paper coated with 74, 75 and 77 spray adhesives specified in Table 2. The mortality of the insects is indicated in Table 6.

At three-hour exposures at light concentrations (0.15–0.18 mg/cm$^2$) of Dri-Die, maximum mortality was 28%. On deposits 14 to 35 days old, it was 4% or less. At heavier concentrations (0.55–0.59 mg/cm$^2$), 100% mortality occurred on deposits up to 14 days old on 74 adhesive. At 24-hour exposures at light concentrations, 100% mortality occurred on deposits up to 35 days old on 74 adhesive.

Thus, heavy concentrations of Dri-Die on 74 adhesive provide the best control for *Tribolium confusum*.

TABLE 6

MORTALITY OF TRIBOLIUM CONFUSUM EXPOSED TO LIGHT (0.15–0.18 MG/CM$^2$) AND HEAVY (0.55–0.59 MG/CM$^2$) DEPOSITS OF DRI-DIE

| | Mean No. Dead* out of 20 | | | | | | | | | |
|---|---|---|---|---|---|---|---|---|---|---|
| | 3 hour exposure | | | | | 24 hour exposure | | | | |
| | Age of deposit (days) | | | | | | | | | |
| | 0 | 7 | 14 | 21 | 35 | 0 | 7 | 14 | 21 | 35 |
| (light dep) 74 | 6 | 1.5 | 1 | 0.3 | 0 | 20.1 | 19.5 | 10 | 10 | 8 |
| (heavy dep) | 20 | 20 | 20 | 17 | 11 | 20 | 20 | 20 | 20 | 20 |
| (light dep) 75 | 5.5 | 1 | 0.5 | 0 | 0 | 20 | 9 | 4.5 | 4 | 4 |
| (heavy dep) | 20 | 18 | 11.5 | 10 | 7 | 20 | 20 | 16.5 | 18 | 8.5 |
| (light dep) 77 | 1 | 0 | 0 | 0 | 0 | 5 | 1.5 | 0 | 1.5 | 0.5 |
| (heavy dep) | 20 | 5 | 3 | 4 | 2 | 18.5 | 20 | 17 | 3 | 2 |

*Figures rounded to nearest 0.5.

It is to be appreciated that the invention is not aimed at controlling all insects known as stored food product pests. Its applications are limited, understandably, to those species that are affected by the insecticidal action of silica gel, specifically silica aerogel, consisting of very fine particles of amorphous silica gel such as described hereinabove.

A most important aspect of the invention is the provision of a suitable substrate/binding means combination ensuring that the release of silica aerogel particles from the substrate does not take place in normal conditions (drafts, natural air convections) until specific forces are applied onto the silica gel particles anchored to the substrate. The bond between the silica gel deposit and the substrate should be of such magnitude, however, that the particles would be released from the substrate, generally, when contacted by insects such as merchant grain beetles (*Oryzaephilus mercator*) or confused flour beetle (*Tribolium confusum*). When the bond is of a suitable strength, the silica gel particles are not detached from the substrate by currents of ambient air, but are released and picked up by the insects. The particles can adhere to mouth, feet or other parts of the insect body, eventually causing the insect's death.

While detailed tests were conducted on the two aforementioned species only, merchant grain beetle and confused flour beetle, it is reasonable to assume that the scope of application of the invention is broader, covering other household species affected by silica aerogel. Other household insects susceptible to the action of silica aerogel are, e.g. cockroaches, silverfish and wood termites. It is the provision of suitable binding means, or adhesive in particular, that ensures the advantageous features of the invention.

While an adhesive is used in the above-described embodiment of the invention, it is also conceivable to provide a suitable bond between the silica gel particles and a substrate using other binding means. An example thereof might be controlled passing of silica gel particles into the surface of a fibrous or porous material, e.g. a plastic.

In the course of experiments, suitable binding agents were selected to meet the goal of the invention, i.e. to provide a bond between the silica gel particles and the substrate such that the silica gel particles do not get swept away off the substrate by usual air currents but can be released off the substrate by forces concomitant with an insect, such as the merchant grain beetle, contacting the device, particularly touching the silica gel particles.

Optionally, but not necessarily, the device may include an insect attractant, e.g. a pheromone or a food attractant or bait.

Food attractants may be mixed with the silica gel, added to the adhesive or impregnated into the substrate.

The device is designed to allow insects to leave the device and not to trap them. The silica gel particles adhering to the insect's body bring about its death through mechanical or biochemical action sometimes many hours after the insect leaves the device.

I claim:

1. A device for controlling stored-food insects, comprising a substrate selected from the group consisting of paper, burlap, cardboard and porous plastic, a layer of non-drying adhesive attached to said substrate and a deposit of silica aerogel particles atop the adhesive layer, the silica aerogel particles being releasable upon the insect contact thereof.

2. A device for controlling stored-food insects comprising a substrate selected from the group consisting of paper, burlap, cardboard and porous plastic to which is secured a double-coated tape consisting of a plastic film and a layer of non-drying adhesive on each side, said tape being secured to the substrate with one adhesive layer and possessing a deposit of silica aerogel particles atop the other adhesive layer.

3. A device according to claim 2 further comprising insect attractants.

4. A device according to claim 1 or 2 wherein the silica aerogel is amorphous silica gel of particle size in the range 0.01–0.05 microns and average size of particle aggregates about 3 microns.

5. A device according to claim 1 wherein the adhesive is a substantially permanent synthetic elastomer adhesive.

6. A device according to claim 1 wherein the adhesive means is a medium firm acrylic adhesive.

7. A device as set forth in claim 2 wherein the bond and/or thickness of the binding means is such as to allow the release of said silica gel particles under conditions occasioned by insects contacting the particles.

8. A device according to claim 2 further comprising insect attractants.

* * * * *